US007751900B2

(12) United States Patent
Voelkel

(10) Patent No.: US 7,751,900 B2
(45) Date of Patent: *Jul. 6, 2010

(54) STIMULATION CHANNEL SELECTION METHODS

(75) Inventor: Andrew W. Voelkel, Venice, CA (US)

(73) Assignee: Advanced Bionics, LLC, Valencia, CA (US)

(*) Notice: Subject to any disclaimer, the term of this patent is extended or adjusted under 35 U.S.C. 154(b) by 152 days.

This patent is subject to a terminal disclaimer.

(21) Appl. No.: 11/498,023

(22) Filed: Aug. 2, 2006

(65) Prior Publication Data
US 2006/0271114 A1 Nov. 30, 2006

Related U.S. Application Data

(62) Division of application No. 10/318,433, filed on Dec. 13, 2002, now Pat. No. 7,130,694.

(60) Provisional application No. 60/344,639, filed on Dec. 26, 2001.

(51) Int. Cl.
A61N 1/36 (2006.01)

(52) U.S. Cl. ........................................................ 607/57

(58) Field of Classification Search ............ 607/45, 607/46, 55–57, 62
See application file for complete search history.

(56) References Cited

U.S. PATENT DOCUMENTS

| 4,267,410 | A | | 5/1981 | Forster et al. |
| 4,408,608 | A | | 10/1983 | Daly et al. |
| 4,424,812 | A | | 1/1984 | Lesnick |
| 4,515,158 | A | | 5/1985 | Patrick et al. |
| 4,532,930 | A | | 8/1985 | Crosby et al. |
| 4,577,641 | A | | 3/1986 | Hochmair et al. |
| 4,612,934 | A | | 9/1986 | Borkan |
| 4,813,417 | A | * | 3/1989 | Soli et al. ............. 607/56 |
| 4,819,647 | A | | 4/1989 | Byers et al. |
| 4,901,353 | A | | 2/1990 | Widin |
| 4,947,844 | A | | 8/1990 | McDermott |
| 4,991,582 | A | | 2/1991 | Byers et al. |

(Continued)

FOREIGN PATENT DOCUMENTS

EP 0241101 B1 10/1987

OTHER PUBLICATIONS

Segel, Overstreet, Kruger and Mishra inventors for AB-313U; U.S. Appl. No. 10/651,653, filed Aug. 29, 2003; entitled "System and Method for Fitting a Cochlear Implant Sound Processor Using Alternative Signals".

(Continued)

Primary Examiner—George R Evanisko
Assistant Examiner—Amanda Patton
(74) Attorney, Agent, or Firm—AdvantEdge Law Group, LLC

(57) ABSTRACT

Methods of selecting a number of channels for stimulation within a neural stimulation system include determining an amplitude of a multiplicity of stimulation signals each corresponding to a channel within a multiplicity of channels in the implantable stimulation system, using the amplitudes of the stimulation signals to determine a probability of each of the stimulation signals, and using the probabilities of one or more of the stimulation signals to randomly select a predetermined number of channels from the multiplicity of channels through which one or more of the stimulation signals are applied to a patient during a stimulation frame.

7 Claims, 8 Drawing Sheets

U.S. PATENT DOCUMENTS

| | | | |
|---|---|---|---|
| 5,095,904 | A | 3/1992 | Seligman et al. |
| 5,271,397 | A | 12/1993 | Seligman et al. |
| 5,522,865 | A | 6/1996 | Schulman et al. |
| 5,571,148 | A | 11/1996 | Leob et al. |
| 5,601,617 | A | 2/1997 | Loeb et al. |
| 5,603,726 | A | 2/1997 | Schulman et al. |
| 5,626,629 | A | 5/1997 | Faltys et al. |
| 5,800,475 | A | 9/1998 | Jules |
| 5,824,022 | A | 10/1998 | Zilberman et al. |
| 5,983,139 | A | 11/1999 | Zierhofer |
| 5,991,663 | A | 11/1999 | Irlicht et al. |
| 6,002,966 | A | 12/1999 | Loeb et al. |
| 6,219,580 | B1 | 4/2001 | Faltys et al. |
| 6,289,247 | B1 | 9/2001 | Faltys et al. |
| 6,308,101 | B1 | 10/2001 | Faltys et al. |
| 6,594,525 | B1 | 7/2003 | Zierhofer |
| 6,728,578 | B1 | 4/2004 | Voelkel |
| 6,996,438 | B1 | 2/2006 | Voelkel |
| 7,043,303 | B1 | 5/2006 | Overstreet |
| 2006/0271113 | A1 * | 11/2006 | Voelkel ............................ 607/2 |
| 2006/0271126 | A1 * | 11/2006 | Voelkel .......................... 607/57 |
| 2006/0271127 | A1 * | 11/2006 | Voelkel .......................... 607/57 |

OTHER PUBLICATIONS

Litvak, Krubsack and Overstreet inventors for AB-354P; U.S. Appl. No. 60/426,267, filed Nov. 13, 2002; entitled "Methods of Using Current Steering to Represent the Within-Channel Fine Structure".

Overstreet, Litvak and Faltys inventors for AB-378P; U.S. Appl. No. 60/425,215, filed Nov. 8, 2002; entitled "Multi-electrode Stimualtion to Elicit Electrically-Evoked Compound Action Potential".

Overstreet inventor for AB-379P; U.S. Appl. No. 60/425,208, filed Nov. 8, 2002; entitled "Method for Generating a Cochlear Implant Program Using Multi-Electrode Stimuation to Elicit the Electrically-Evoked Compound Action Potential".

* cited by examiner

STIMULATION CHANNEL SELECTION METHODS

RELATED APPLICATIONS

The present application is a divisional application of U.S. application Ser. No. 10/318,433, filed Dec. 13, 2002 now U.S. Pat. No. 7,130,694, which application claims the benefit of Provisional Application Ser. No. 60/344,639, filed Dec. 26, 2001 and its Appendix. Both applications, including the Appendix of Provisional Application Ser. No. 60/344,639, are incorporated herein by reference in their entireties.

BACKGROUND

Hearing loss may be due to many different causes, but is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information, in the form of pressure waves, reaches the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to convert acoustic signals into auditory nerve impulses. People with sensorineural hearing loss are unable to derive any benefit from conventional hearing aid systems, no matter how loud the acoustic stimulus is made, because their mechanisms for converting sound energy into auditory nerve impulses have been damaged. Thus, in the absence of properly functioning hair cells, auditory nerve impulses are not generated directly from sounds.

To overcome sensorineural deafness, numerous Implantable Cochlear Stimulation (ICS) systems—or cochlear prosthesis—have been developed. Such systems seek to bypass the hair cells in the cochlea by presenting electrical stimulation to the auditory nerve fibers directly, leading to the perception of sound in the brain and at least a partial restoration of hearing function. The common denominators in most ICS systems have been the implantation of electrodes into the cochlea, and a suitable external source of an electrical signal for the electrodes.

An ICS system operates by direct electrical stimulation of the auditory nerve cells, bypassing the defective cochlear hair cells that normally convert acoustic energy into electrical activity in the nerve cells. In order to effectively stimulate the nerve cells, the electronic circuitry and the electrode array of the ICS system perform the function of separating the acoustic signal into a number of parallel channels of information, each representing the intensity of a narrow frequency band within the acoustic spectrum. Ideally, the electrode array would convey each channel of information selectively to the subset of auditory nerve cells that normally transmit signals within that frequency band to the brain. Those nerve cells are arranged in an orderly tonotopic sequence, from high frequencies at the basal end of the cochlear spiral to progressively lower frequencies towards the apex, and ideally the entire length of the cochlea would be stimulated to provide a full frequency range of hearing. In practice, this ideal is not achieved, because of the anatomy of the cochlea which decreases in diameter from the base to the apex, and exhibits variations between patients. Because of these difficulties, known electrodes can at best be promoted to the second turn of the cochlea.

The signal provided to the electrode array is generated by a signal processing element of the ICS system. In known ICS systems, the acoustic signal is processed by a family of parallel Bandpass (BP) filters, or the equivalent, resulting in M stimulation channels. Generally, the important information for speech understanding is contained in subset of all the M channels. This subset is usually made up of the channels containing the highest amplitude signals among the M channels at any given time. One common stimulation strategy selects N of the M channels for stimulation based on the amplitude of the signals in the channels. There are at least two advantages to the N out of M (N-of-M) strategy. First, an N-of-M strategy allows higher stimulation rates for a given pulse width when using non simultaneous stimulation. Second, an N-of-M strategy performs a data reduction function, in that BP channels that contain lower amplitude information are effectively muted, limiting their contribution to electrode interaction problems.

But, there are potential disadvantages to N-of-M strategies as well. The data reduction function of a standard N-of-M strategy is implemented using an all or nothing algorithm, selecting only the channels with the highest amplitude signals in a given stimulus frame. This means that all information in the lower amplitude channels is lost during that frame. This could be very disadvantageous in situations where the overall frequency distribution remains relatively constant for a period of time, such as when listening in certain noisy environments or detecting background sounds during vowels. One example of this would be someone honking a horn while someone is talking. If the horn is loud enough, its spectral content would overwhelm the talker, and the standard N-of-M decision matrix would only deliver envelope information to the pulse generator for those channels which contain "horn content". All of the other channels would be effectively muted.

What is needed is a method for processing the channels of an ICS system, which method provides the advantages of an N-of-M stimulation strategy, without muting channels having low to moderate signal amplitudes.

SUMMARY

Methods of selecting a number of channels for stimulation within a neural stimulation system include determining an amplitude of a multiplicity of stimulation signals each corresponding to a channel within a multiplicity of channels in the implantable stimulation system, using the amplitudes of the stimulation signals to determine a probability of each of the stimulation signals, and using the probabilities of one or more of the stimulation signals to randomly select a predetermined number of channels from the multiplicity of channels through which one or more of the stimulation signals are applied to a patient during a stimulation frame.

BRIEF DESCRIPTION OF THE DRAWINGS

The above and other aspects, features and advantages of the present systems and methods will be more apparent from the following more particular description thereof, presented in conjunction with the following drawings wherein.

Corresponding reference characters indicate corresponding components throughout the several views of the drawings.

DETAILED DESCRIPTION

Figure 1:
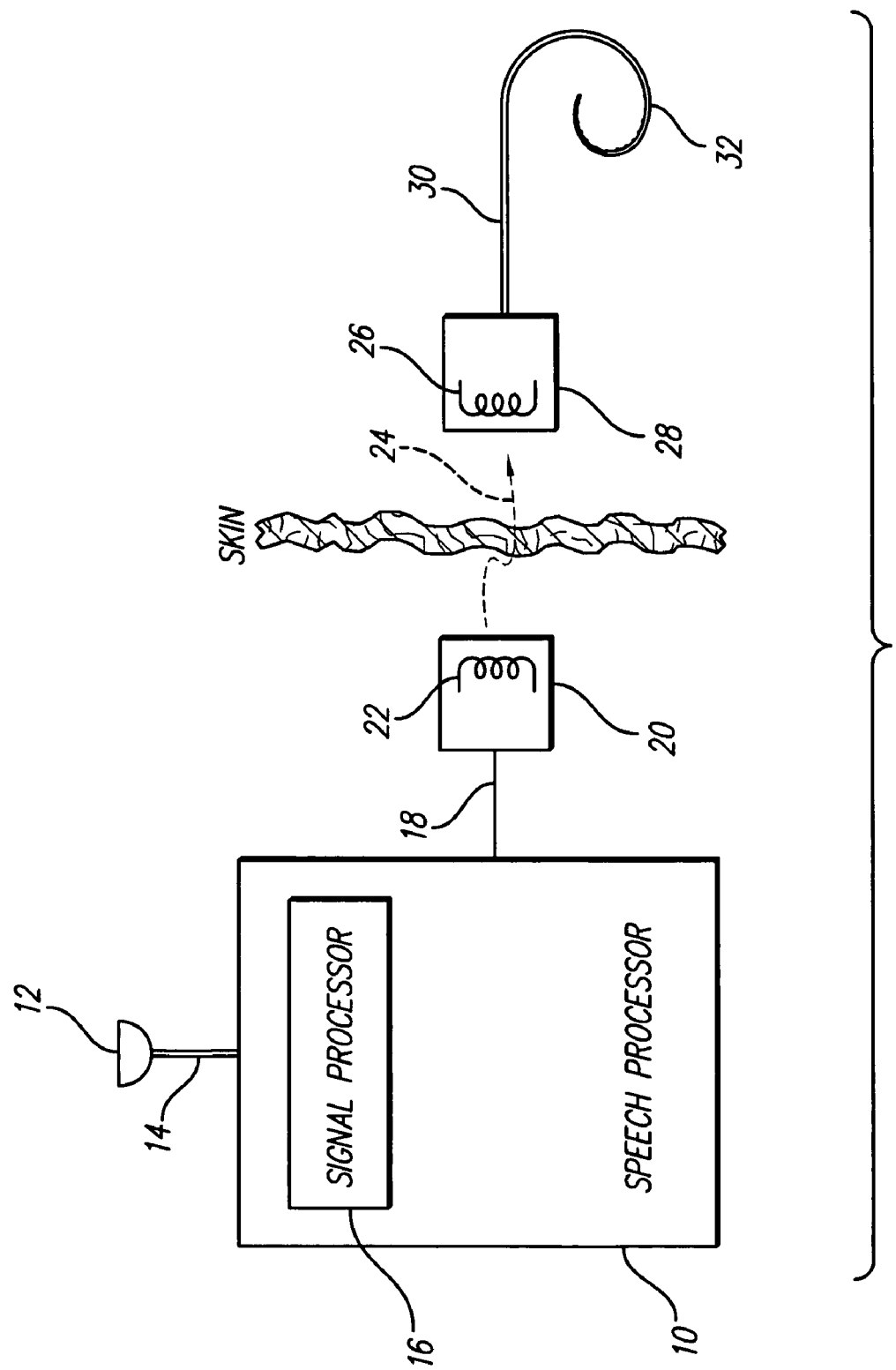
FIG. 1 shows the major elements of a known Implantable Cochlear Stimulation (ICS) system.

Improved pulse skipping strategies for implantable neural stimulation systems are described herein. In some examples, the methods and systems described herein select N out of M (N-of-M) channels for stimulation during a stimulation frame. A microphone transduces acoustic energy into an electrical signal. The electrical signal is processed by a family of bandpass filters, or the equivalent, to produce M frequency channels. In an exemplary embodiment, a probability based channel selection strategy computes a probability for each of the M channels based on the envelope amplitude of the signal on each channel. N of the M channels are probabilistically selected for stimulation based on their individual probability. The result is a randomized "stochastic" stimulus presentation to the patient.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

In accordance with one aspect of the present methods and systems, there is provided a probability based N-of-M stimulation strategy. Such randomized stimulation advantageously reduces "under representation" of weak channels for steady state input conditions, such as vowels.

In some examples, the present methods and systems provide more natural stimulation to the user. Naturally occurring nerve firing patterns tend to exhibit random behavior. Randomizing the selection of channels providing stimulation better matches the naturally occurring patterns. Further, random selection of channels tends to eliminate adverse effects that result from a more strictly periodic stimulus, such as the tendency for certain patients to detect the carrier.

The methods and systems described herein also provide a capability to emphasize specified channels. For example, when a transient condition is detected, channels carrying high frequency signals may be given a preference in the N out of M selection process, thereby emphasizing the high frequency content of the transient. Parameters of the transient detection process and the selection criteria of high frequency channels may be tuned to a particular user during ICS fitting.

The methods and systems described herein also reduce processing requirements compared to known bubble sorting methods. A running threshold is maintained. At each stimulation frame, the amplitude of each channel is compared to the threshold, and channels with amplitudes exceeding the threshold are selected for stimulation. A variable "J" is set to the number of channels selected. The threshold is increased if "J" is greater than N, and the threshold is decreased if "J" is less than N, thus controlling the number of channels selected. Because this technique does not use an expensive bubble sort operation, it saves processor resources, which extends the battery life of the SCS system.

The present methods and systems relate to multi-channel implantable neural stimulation systems, and more particularly to a probabilistic technique for selecting which channels of the multi-channel neural stimulation system are to be selected for providing stimulation based on a given input signal. While the present methods and systems are described in connection with an implantable cochlear stimulation (ICS) system, it is to be understood that the present methods and systems is not limited for use only in ICS systems. Rather, the present methods and systems may find applicability in many types of neural stimulation systems where multi-channel stimulation is provided, including spinal cord stimulation systems, deep brain stimulation systems, and other neural stimulation systems.

A probabilistic pulse skipping strategy for Implantable Cochlear Stimulation (ICS) systems selects N out of M (N-of-M) channels for stimulation during a given stimulation frame. A functional diagram of a typical ICS system is shown in FIG. 1. The ICS system includes a speech processor 10 that could be a Wearable Speech Processor (WP), a Behind-The-Ear (BTE) speech processor, an implantable speech processor of a fully implantable cochlear stimulation system, or any signal processor that is used to process acoustic signals for use by an ICS system. By way of overview, a microphone 12 is electrically connected to a speech processor 10 by a first wire 14, or may be attached to the speech processor 10 as in the case of known BTE speech processors. The microphone 12 may also, in some embodiments, be coupled to the speech processor 10 via a wireless link.

The microphone 12 converts acoustic energy into an electrical signal for subsequent processing. The speech processor 10 contains a signal processor 16 that processes the electrical signal from the microphone 12. The output signal of the signal processor 16 is carried by a second wire 18, or equivalent link, to a headpiece 20 carried on the patient's head. A first (or primary) coil 22 receives the output signal and transmits it as a control signal 24 from the headpiece 20 to implantable electronics 28. The implantable electronics 28 include a second (or secondary) coil 26 for receiving the control signal 24.

The implantable electronics 28 processes the control signal 24 and derives therefrom the information needed in order to generate a stimulation current that is provided through a lead 30 to one or more of electrodes of the electrode array 32. The electrode array 32 comprises a multiplicity of electrodes. The electrode array 32 is implanted in the patient's cochlea.

The architecture of ICS systems may vary. The ICS system may include a wearable speech processor that is worn on the users belt and is connected to a microphone and a headpiece by wiring, or a Behind-The-Ear (BTE) speech processor resembling a typical hearing aid, that is worn behind the patient's ear and retained by an earhook. Another example is a fully implantable ICS system in which a speech processor 10 is integrated into an implantable device. Those skilled in the are will recognize that all of these variations include similar signal processing, and that all of these variations benefit from the present methods and systems, as described below, and are intended to come within the scope of the present methods and systems.

Figure 2:
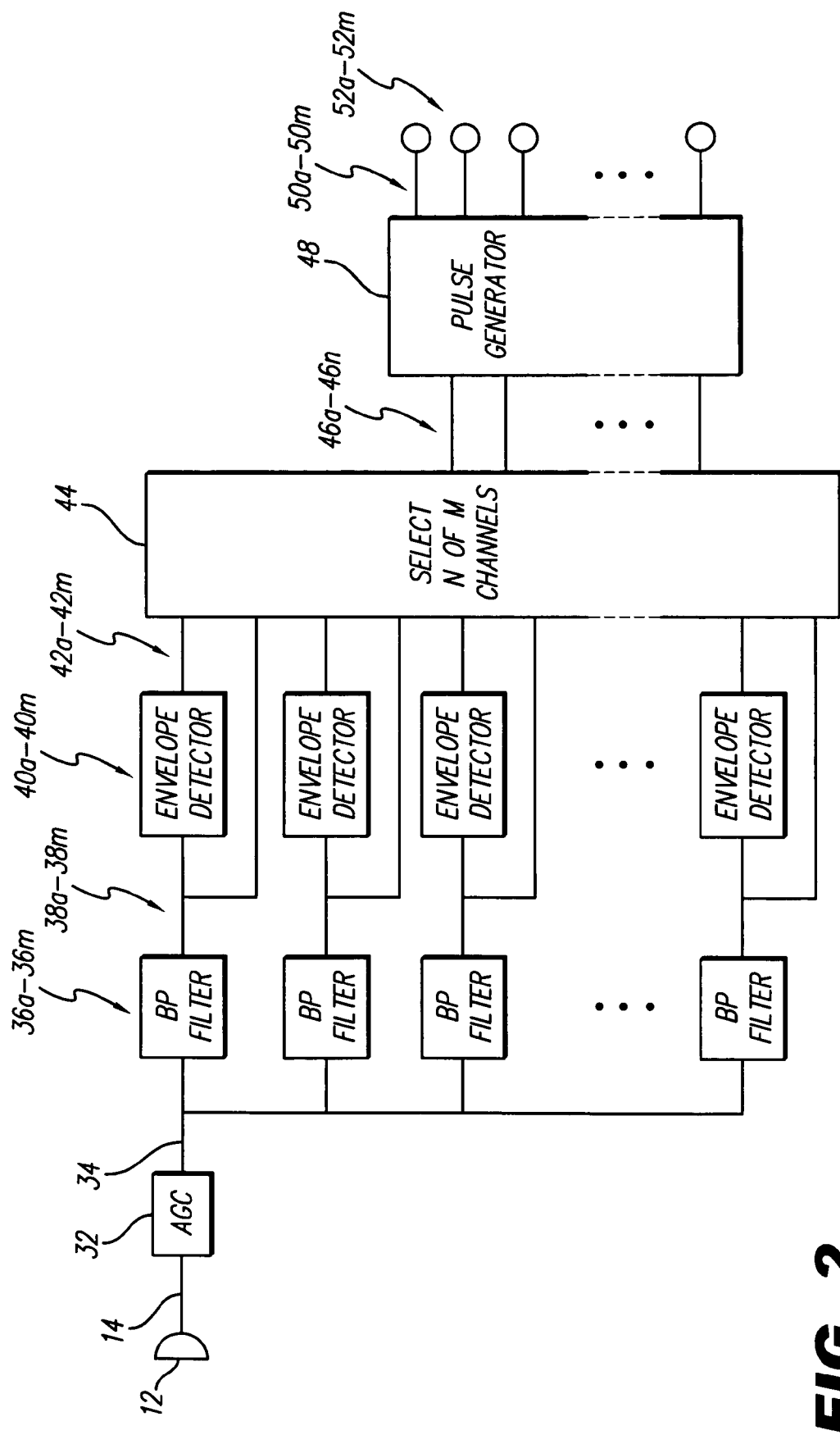
FIG. 2 shows a block diagram of the N out of M (N-of-M) processing.

A functional block diagram of an ICS system that includes an N out of M pulse skipping strategy is shown in FIG. 2. The microphone 12 is connected by the first signal path 14 to an Automatic Gain Control (AGC) circuit 32 in the signal processor 10. The output 34 of the AGC circuit is input to M Bandpass Filters (BPF) 36a-36m having output channels 38a-38m. The BPF output channels 38a-38m are input to respective envelope detector circuits 40a-40m. The BPF output channels 38a-38m, and the envelope output signals 42a 42m, are provided to processing circuitry 44 that selects N out of M channels. The Select-N-out-of-M-Channels circuit 44 thus provides N channels selected for stimulation, 46a-46n, to a Pulse Generator 48. Leads 50a-50m respectively connect electrodes 52a-52m to the Pulse Generator 48. However, stimulation signals are present only on N of the M leads, which N leads correspond to the N channels selected for stimulation 46a-46n.

The functional diagram in FIG. 2 includes functions that may be used in the pulse skipping strategy. Those skilled in the art will recognize that the signal processor typically performs other signal processing functions not shown (e.g., compressive mapping, determination and provision of power, etc.). A more complete description of the main functions performed by a typical ICS system may be found in U.S. Pat. No. 6,219,580 and/or U.S. Pat. No. 6,308,101, both of which patents are incorporated herein by reference. Moreover, those of skill in the art will appreciate that the functional block diagram of FIG. 2 illustrates just one architecture—dividing the incoming signal into frequency bands, and processing each band in parallel—that may be used in a cochlear implant system. The present methods and systems are not limited to such architecture, but rather relates to the way N of M channels are selected, e.g., to the function that is carried out in the "Select N of M Channel" box 44 shown in FIG. 2. The circuitry that precedes and follows the box 44 is not central to the present methods and systems, and may be achieved in numerous ways.

Figure 3:
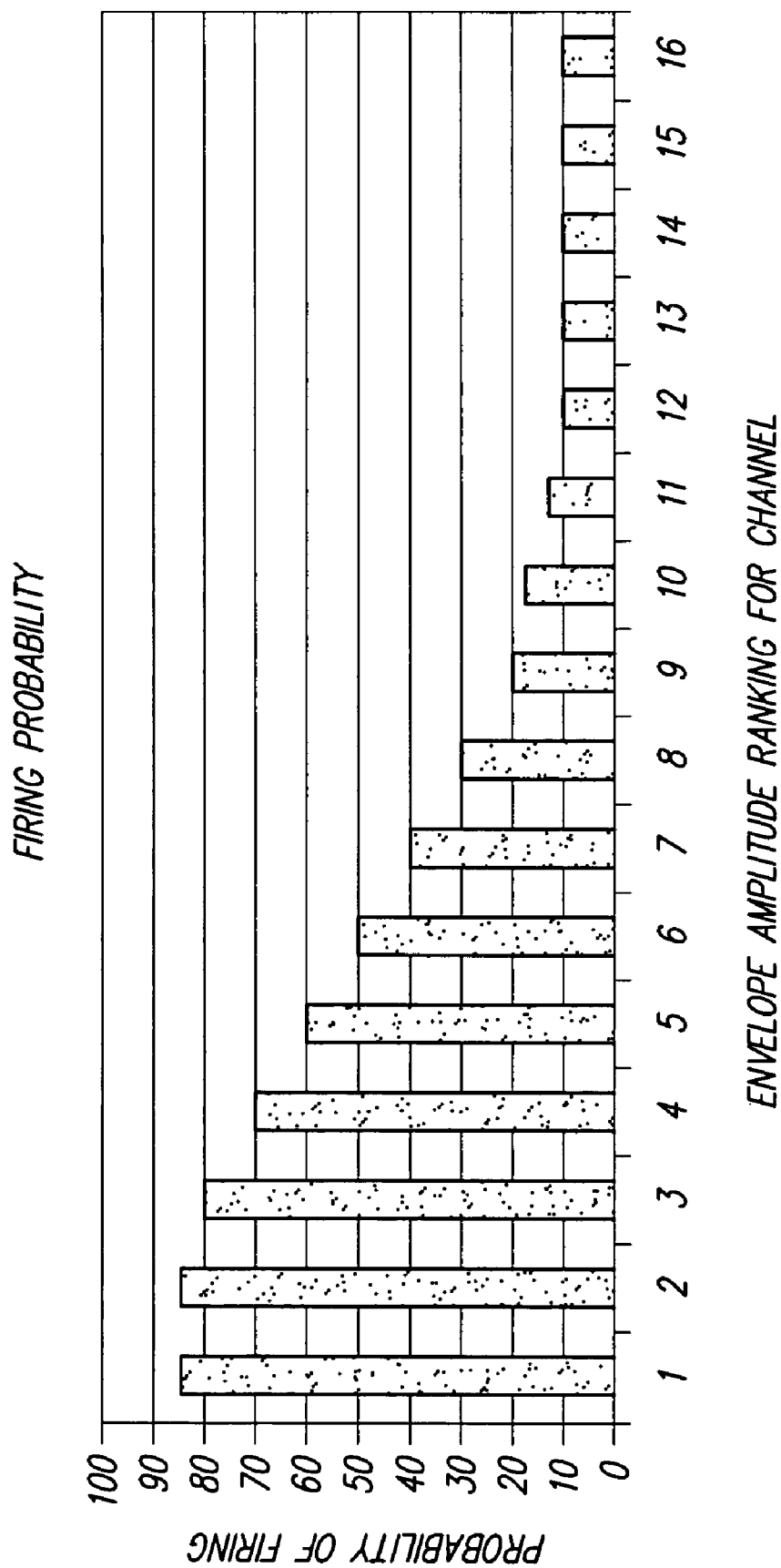
FIG. 3 depicts a plot of channel probability versus channel number, arranged by decreasing probability.

A first embodiment of an improved pulse skipping strategy includes the use of a discrete probability function. An example of a probability function for a strategy where N=6 and M=16 is shown in FIG. 3. The probabilities of the 16 channels are scaled so that the sum of the probabilities of the 16 channels is 6. As a result, the average probability in this example is 6/16. The 16 channels are compared to random numbers from a uniform distribution between zero and one, one channel at a time. For example, if a channel has a scaled probability of 0.85, and the random number provided for the comparison is less than 0.85, the channel will be selected for stimulation (i.e., the channel will be selected 85% of the time.) Similarly, a channel with a probability of 0.10 will be selected 10% of the time. The random numbers are unique for each comparison, and may be obtained through table look-up, a random number generator, or from some other method of obtaining random numbers. Any method of obtaining the random numbers may be used.

Channel selection is complete when N channels (6 channels in the example) have been selected for stimulation for a given frame. The order in which the probabilities of the channels are compared to a random number may be randomized to provide an opportunity for low probability channels to be selected, or some other method of determining an order for channel selection may be utilized.

Figure 4:
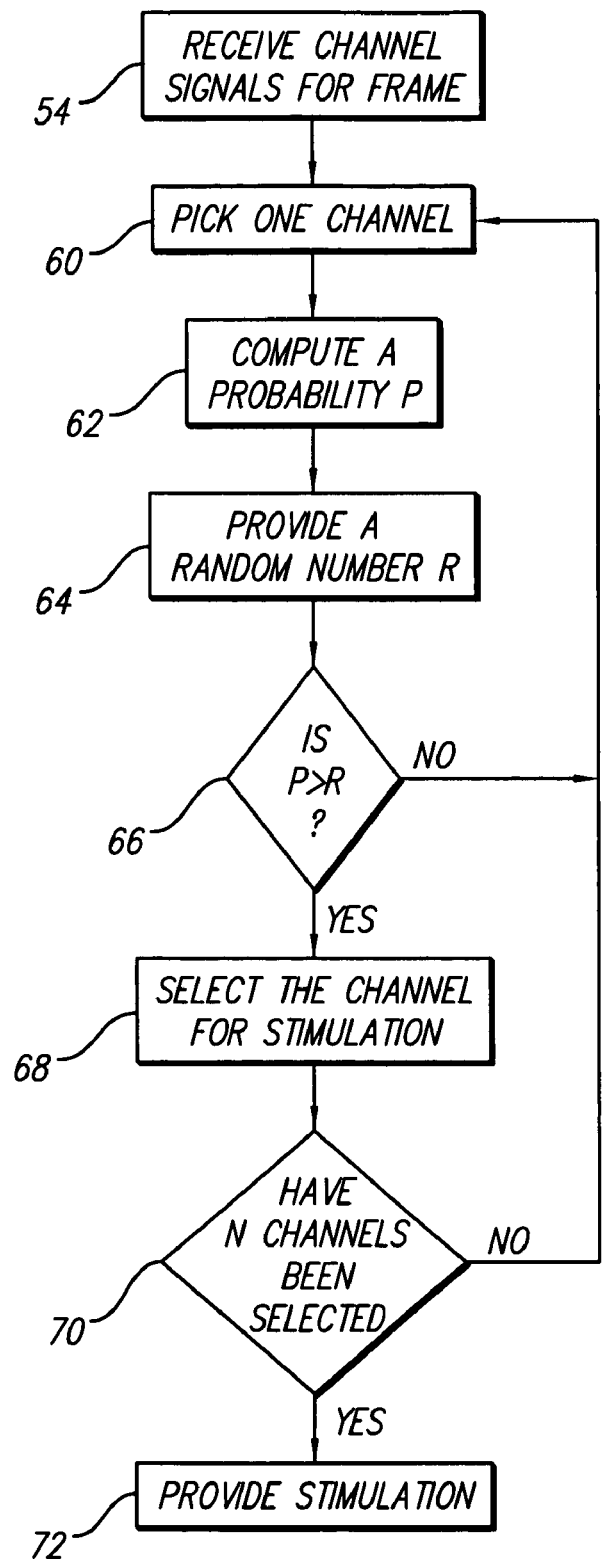
FIG. 4 shows a flow chart for a probabilistic N-of-M channel selection method.

A flow chart of the steps comprising the probabilistic pulse skipping strategy described above is shown in FIG. 4. In FIG. 4, each main step of the strategy is represented as a "block", having a reference number. As seen in FIG. 4, the M channel signals for a frame are received (block 54). There is an amplitude associated with each of the M channel signals. One of the M channels is selected for further processing (block 60). In some examples, a method for picking a channel is utilized that allows representation of all channels, e.g., the channels may be selected randomly. A probability "P" for the picked channel is then computed (block 62) as described above in connection with FIG. 3. For example, the probability may be computed as N/M weighted by the amplitude of the signal. A random number "R" is also generated (block 64), as also described above in connection with FIG. 3. A determination is then made as to whether "P" is greater than "R" (block 66).

If the probability "P" is less than the random number "R", then that channel is not selected as one of the N channels selected for stimulation during the frame (block 68). A new channel is then picked (block 60) and the process of computing a probability "P" (block 62) and providing a random number "R" (block 64) and comparing the probability "P" of the selected channel to the random number "R" (block 66) is repeated.

If the probability "P" is greater than the random number "R", then that channel is selected to be one of the N channels selected for stimulation during the frame (block 68).

A determination is next made as to whether N channels have been selected (block 70) for stimulation during the frame. If less than N channels have been selected for stimulation, a new channel is picked (block 60) and the process of computing a probability "P" (block 62) and providing a random number "R" (block 64) and comparing the probability "P" of the selected channel to the random number "R" (block 66) and selecting the channel for stimulation (bock 68) is repeated. When N channels have been selected for stimulation, the process is complete, and stimulation may be provided (block 72).

There are at least two differences between a probabilistic pulse skipping N-of-M strategy and known N-of-M strategies. First, consider the situation where the dominant spectral cues are completely static (an example of this would be someone honking a horn while someone is talking). If the dominant static spectral cues are loud enough (i.e., if the horn is loud enough), the spectral content of the static cues would overwhelm the talker, and the standard N-of-M decision matrix would only select channels for stimulation that contain the dominant static spectral cues, i.e., that contain "horn content". All of the other channels would be effectively muted. However, when the probability function of the random pulse skipping N-of-M strategy of the present methods and systems are employed, the weaker channels would still deliver stimulus to the patient, albeit at a lower rate than the strong channels. This is a substantial advantage in certain listening environments, especially noisy environments.

Second, the random pulse skipping N-of-M strategy of the present methods and systems randomizes the stimulus to any channel to a certain extent. Randomized stimulus may be more natural in that is it similar to nerve firing patterns that occur naturally. Also, a randomized stimulus tends to eliminate adverse effects that result from a more strictly periodic stimulus, such as the tendency for certain patients to detect the carrier.

The randomization shown in FIG. 3 is not as pronounced as it might be. If the distribution of the firing probabilities were flatter, there would be more randomization and less channel reduction (less emphasis of the strong spectral channels).

However, if N is lowered, and the Firing Probability Curve linearly adjusted to reflect this, the randomization is increased without affecting the extent of the channel reduction. N can be lowered without under representing the bulk of the stimulus channels. The result is a highly randomized stimulus that represents all the channels, yet emphasizes the stronger ones.

In a second embodiment of the present methods and systems, a relatively simple alternative to known N-of-M strategies is utilized that comprises comparing the channel signal amplitudes with a first threshold. In each frame, all the amplitudes are compared with the first threshold. Channels with amplitudes above the first threshold are selected for stimulation. The first threshold is not constant, and may be adjusted after every frame. If more than N channels are above the first threshold in a frame, the first threshold used for the next frame is raised by a certain amount. If less than N channels are above the first threshold, the first threshold used for the next frame is lowered by a certain amount. In this way, the first threshold is dynamically adjusted to a point where an average of N channels will be selected for stimulation per frame.

However, because there is no guarantee that exactly N channels will meet this criteria during any given frame, a method is required to adjust the channel selection so that N channels are selected. There are many ways to ensure that exactly N channels are selected for stimulation. If more than N channels are initially selected for stimulation, high frequency or low frequency channels may be given precedence when selecting channels (for example, selecting the N highest frequency channels that exceed the first threshold, or selecting the N lowest frequency channels that exceed the first threshold). Alternatively, channels may be randomly de-selected from the group of channels that exceed the first threshold, until a total of N channels remain selected for stimulation. As another approach, when the number of channels selected for stimulation for a given frame far exceeds the number N, the channels may be sorted by amplitude. Sorting by amplitude in these limited cases would give a more conventional result, while generally only requiring a sort during transients.

In the case where less than N channels exceed the first threshold, additional channels may be selected from the channels with amplitudes that failed to exceed the first threshold based on frequency (for example, selecting the additional channels from the highest frequency channels with amplitudes that failed to exceed the first threshold, or selecting the additional channels from the lowest frequency channels that failed to exceed the first threshold.) Alternatively, additional channels may be randomly selected from the channels with amplitudes that failed to exceed the first threshold, until a total of N channels are selected for stimulation.

Figure 5:
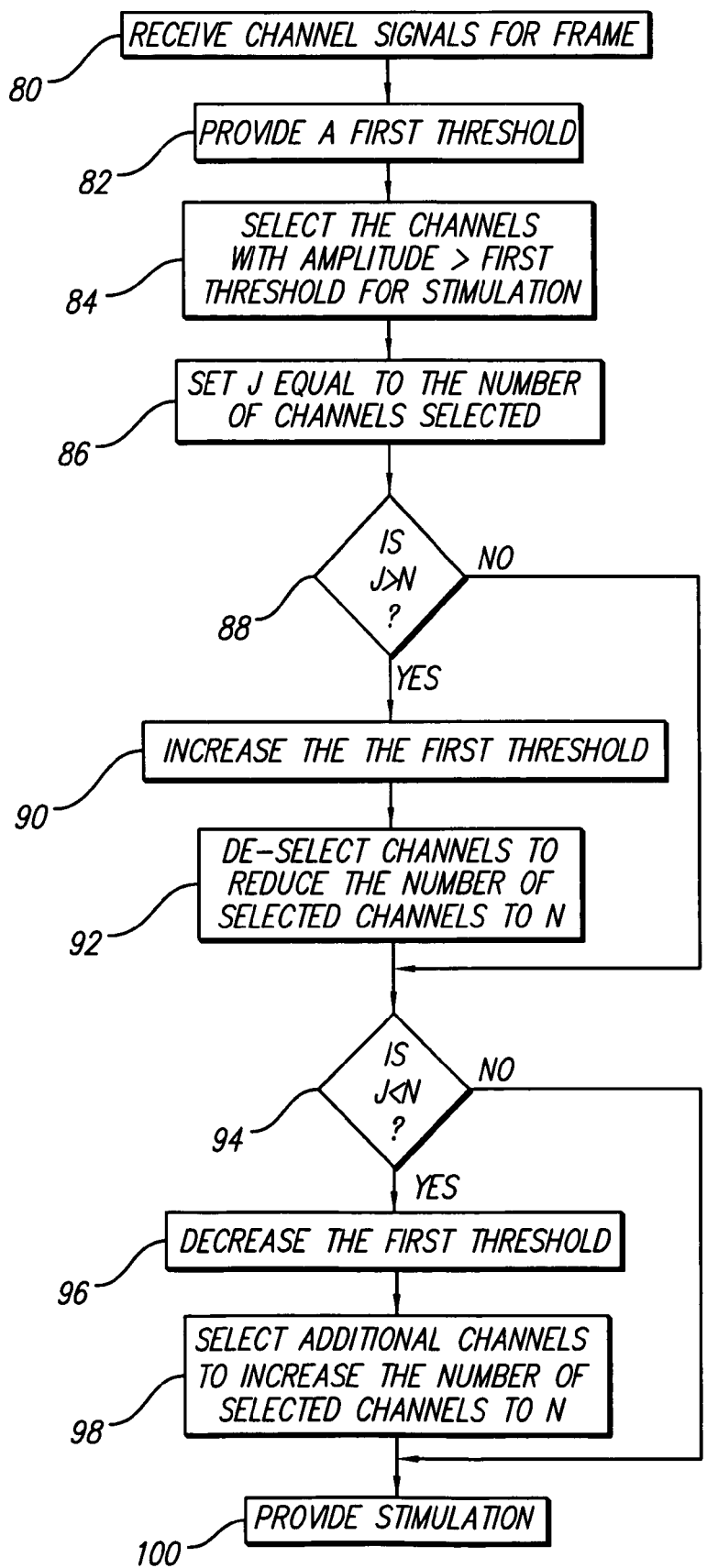
FIG. 5 shows a flow chart for an adjustable threshold based N-of-M channel selection method.

A flow chart of the second embodiment of the present methods and systems is shown in FIG. 5. As a first step, the channel signals for the frame are received (block 80). A first threshold is then provided (block 82), which may be either a stored initial value of the first threshold, or a value of the first threshold recursively computed (e.g., at blocks 90 or 96, as explained below). Next, the channels having an amplitude greater than the first threshold are selected for stimulation (block 84). A parameter "J" is then set to be equal to the number of channels selected (block 86). A determination is then made as to whether "J" is greater than "N" (block 88). If more than "N" channels were selected for stimulation, the first threshold is increased (block 90) for the next frame, and channels are de selected to reduce the total number of channels selected for stimulation to the number "N" (block 92). Exemplary methods for increasing the threshold, and for choosing channels to de-select, may be as described above.

If "J" is smaller than "N" (block 94), then a determination is made to determine if less than "N" channels were selected for stimulation. If less than "N" channels were selected for stimulation, the first threshold is decreased (block 96) for the next frame, and additional channels are selected until "N" channels have been selected (block 98). Exemplary methods for decreasing the threshold, and for choosing additional channels to select for stimulation, may be as described above.

Stimulation is then provided on the "N" channels that have been selected (block 100).

A third embodiment of an improved pulse skipping strategy in accordance with the present methods and systems combines a probability based pulse skipping strategy and a second threshold based pulse skipping strategy. In accordance with this embodiment, an adjusted amplitude is computed for each channel by subtracting a second threshold (in dB) from the amplitude (in dB) of each channel. The adjusted amplitude is mapped into a probability based on the mapping shown in FIG. 6. The greater the adjusted amplitude (in dB), the higher the probability of the channel will be, and the more likely it is that the channel will be selected for stimulation during the frame. As a result, there is no "yes-or-no" decision about whether to select the channel as in the second embodiment, and there is no discontinuity in the selection function. Channels with amplitudes that are significantly higher than the second threshold will be proportionally more likely to be selected for stimulation.

Figure 6:
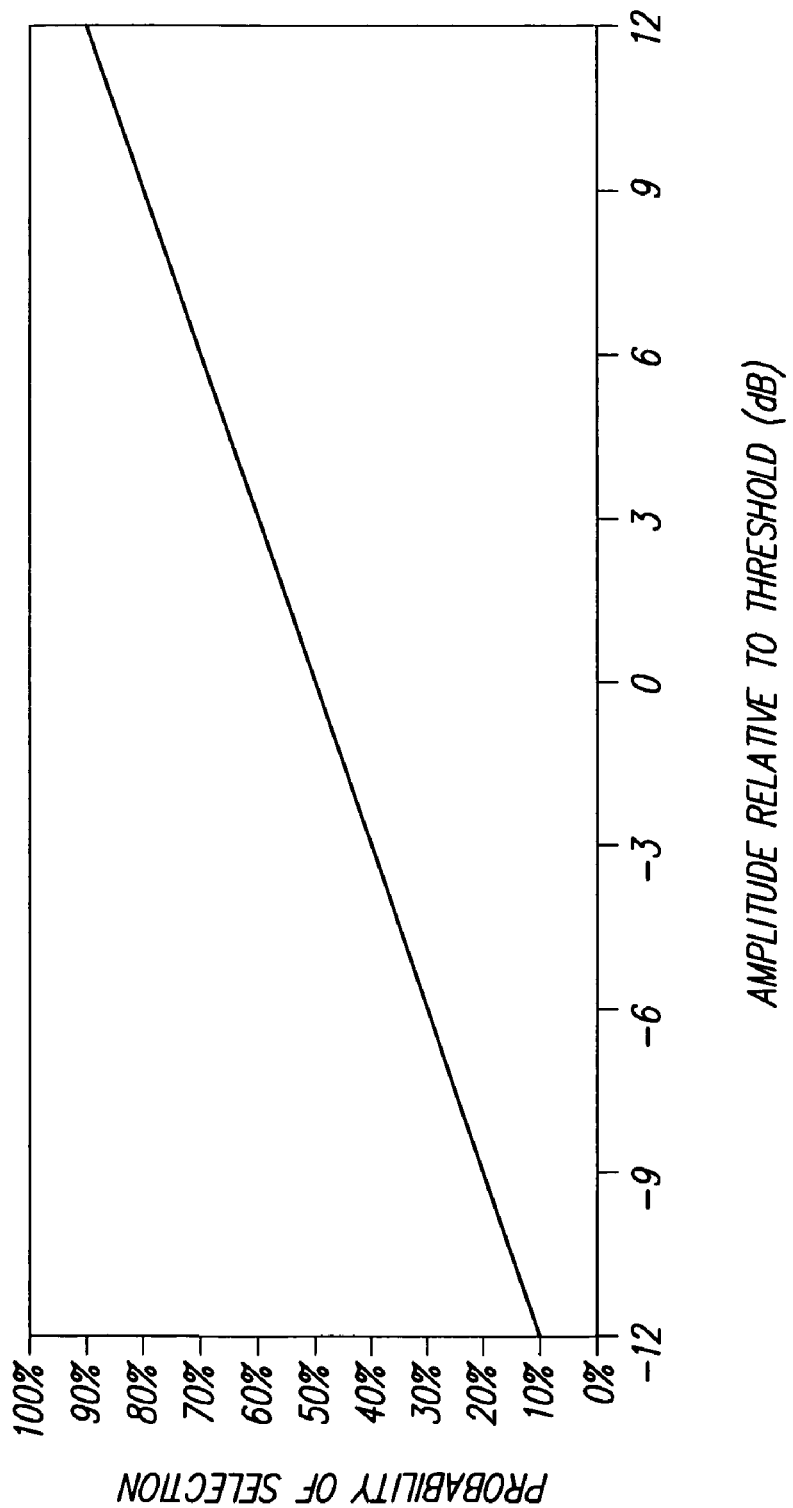
FIG. 6 graphically depicts a mapping from an amplitude to a probability-of-selection for a combination of probability and threshold based N-of-M channel selection method.
Figure 7:
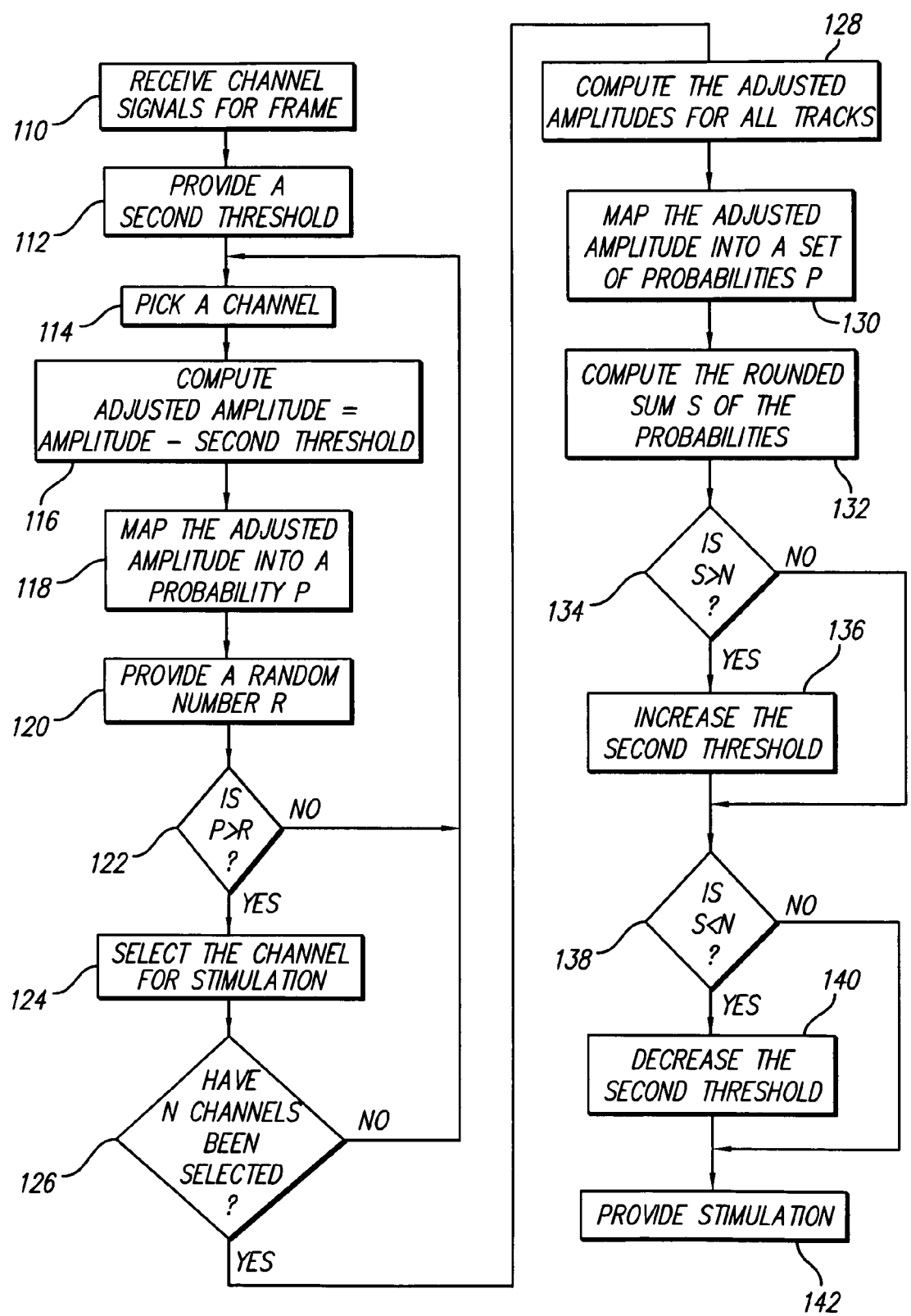
FIG. 7 shows a flow chart for the combination probability and threshold based N-of-M channel selection method.

A flow chart of the third embodiment is shown in FIG. 7. As seen in FIG. 7, for each frame of data, the channel signals are received (block 110). A second threshold is next provided (block 112) that is either a stored initial value of the second threshold, or the second threshold recursively computed (as explained below). A loop is then entered which is executed once for each channel. Upon entering the loop, a channel is picked (block 114) that has not been tested for selection during the present frame. The picked channel includes an amplitude, which is computed as one of several possible measures of the amplitude of the signal on the picked channel, and may include an envelope signal. An adjusted amplitude is then computed (block 116) as the amplitude of the picked channel minus the second threshold (in dB). The adjusted amplitude is then mapped into a probability "P" (block 118) using an appropriate mapping scheme, such as the mapping relationship shown in FIG. 6. A random number "R" is then provided (block 120), e.g., by looking up a random number in a table, by generating a random number using a random number generator, or by some other means. Such random number is uniformly distributed between zero and one.

Still with reference to FIG. 7, a determination is next made as to whether "P" is greater than "R" (block 122). If the probability "P" is greater than the random number "R", the picked channel is selected for stimulation (block 124), and a determination is made as to whether all "N" channels have been selected (block 126). If (at block 122) the probability "P" is not greater than the random number "R", then another channel is picked (block 114) for testing and the loop begins again. The above-described loop (comprising blocks 114-126) is then repeated as required until "N" channels have been selected for stimulation.

Continuing with FIG. 7, once N channels have been selected for stimulation, the second threshold may be adjusted, if necessary. This is done by computing the adjusted amplitudes for all channels (block 128), and then mapping the adjusted amplitude into a set of probabilities P (block 130), as was done previously (at blocks 118 and 120). Next, a rounded sum "S" of the probabilities is computed (block 132) by summing the probabilities, and rounding the sum to nearest integer. A determination is then made as to whether the rounded sum "S" is greater than "N" (block 134), and if so, the second threshold is increased (block 136). Similarly, a determination is made as to whether the rounded sum "S" is less than "N" (block 138), and if so, the second threshold is decreased (block 140). Once the second threshold has been adjusted, either increased (block 136) or decreased (block 140), the stimulation is provided on the selected "N" channels (block 142).

Figure 8:
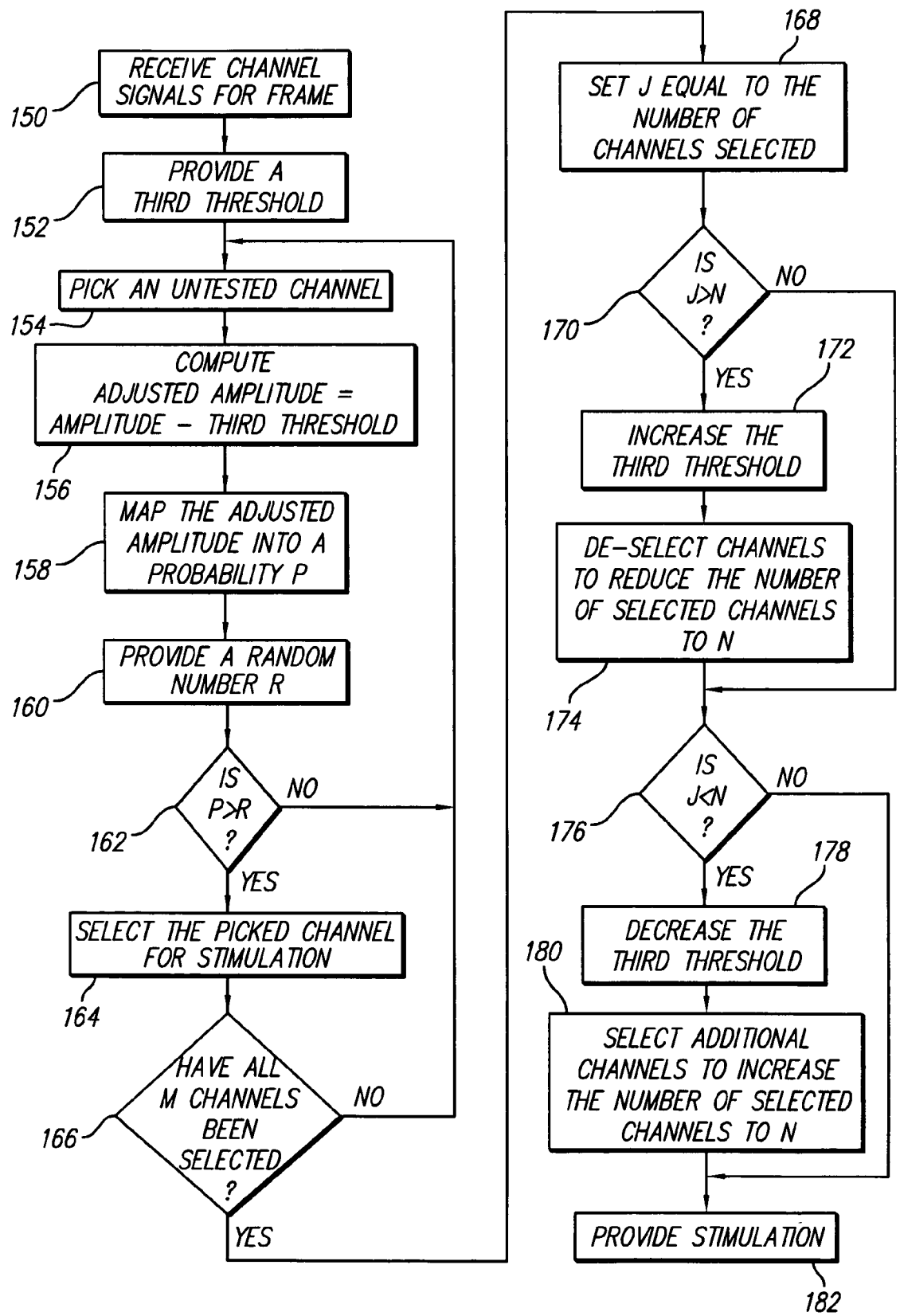
FIG. 8 shows a flow chart of a second embodiment for the combination probability and threshold based N-of-M channel selection method.

A flow chart of a fourth embodiment of the present methods and systems is illustrated in FIG. 8. The fourth embodiment utilizes the same mapping of a signal amplitude in dB into a probability as used in the third embodiment, but exercises a different channel selection process. As seen in FIG. 8, channel signals for the current frame are received (block 150). A third threshold is provided (block 152), which third threshold may be either a stored initial value, or a third threshold recursively computed, as explained below. A loop is then entered which is executed once for each channel. In the loop, an untested channel is selected (block 154). The picked channel includes an amplitude, which may be computed as one of several possible measures of the amplitude of the signal on the picked channel, and may include an envelope signal. The amplitude of the picked signal is then adjusted (block 156). The adjusted amplitude may be computed as the channel amplitude minus the third threshold. The adjusted amplitude is then mapped (e.g., by using the mapping shown in FIG. 6) into a probability "P" (block 158). Then, a random number "R" is provided (block 160). The random number may be derived from a random number look up table, or may be generated using any other appropriate means. The random number should be uniformly distributed between zero and one.

Next, a determination is made as to whether "P" is greater than "R" (block 162). If not, a new untested channel is selected (block 154) and the loop begins again. If "P" is greater than "R", then the picked channel is selected for stimulation (block 164). A determination is then made as to whether all "M" channels have been tested (block 166), thereby assuring that all of the channels have had an opportunity to be selected for stimulation. If not, then the loop begins again (at block 154) for each untested channel.

After all of the channels have had an opportunity to be selected for stimulation, further processing is performed to ensure that exactly N channels are selected, and to adjust the third threshold if more or less than N channels have been selected. To do this, a parameter "J" is set equal to the number of channels selected for stimulation (block 168) and a determination is made as to whether J is equal to "N", the number of channels that should be selected for stimulation in the frame (block 170). If "J" is greater than "N", then more than "N" channels were selected for stimulation, and the value of the third threshold is increased (block 172) for use in subsequent frames. Channels are then de selected to reduce the total number of channels selected for stimulation to the number "N" (block 174). The methods for increasing the third threshold, and for choosing channels to de-select, may be the same as those described in connection with the second embodiment above.

If "J" is less than "N" (block 176), then fewer than "N" channels were selected for stimulation, and the value of the third threshold is decreased (block 178) for use in subsequent frames. Additional channels are then selected to increase the total number of channels selected for stimulation to the number "N" (block 180). The methods for decreasing the third threshold, and for choosing additional channels to select for stimulation, may be the same as those described above in connection with the description of the second embodiment. Stimulation is then provided on the selected channels (block 182).

In the manner described above, and as shown in FIG. 8, the third threshold is recursively adjusted, either by increasing its value (block 172), or by decreasing its value (block 178).

It is noted that the second and fourth embodiments described above may have useful effects during transients, such as would occur during consonants in speech. By modifying the channel selection criteria, certain channels may be emphasized under these conditions. For example, if preference is given to high frequency channels when more than N channels are above the threshold, the high frequency content of transients will be emphasized. This is in contrast to the probabilistic selection process of the first and third embodiments described above, which tend to emphasize all of the input channels equally during a transient. Using either of these approaches during transients may improve hearing, and the results will vary depending on the particular patient. These and other methods may be explored during the patient fitting process, and the methods that provide the best performance can be programmed into the ICS system for each patient.

Much is known about human hearing and its non-linear behavior. Human hearing is known to be more sensitive to certain frequency ranges, and it is known that the sensitivity curves may change with volume. There are many frequency and time-based masking effects. Much of this behavior may be incorporated into the selection of channels for stimulus. Imitating functions that are present in normal hearing may prove to be very helpful. Advantageously, the present methods and systems allow such imitations to be more readily achieved.

As a simple example, the Amplitude Relative to Threshold vs. Probability of Selection relationship shown by the curve in FIG. 6 may be different for each channel, depending on the center frequency of the channel. Differences in the center point of this curve would produce a pre-emphasis curve across the spectrum, resulting in a greater likelihood of selection for channels with certain center frequencies. Changing the slope of these curves would change the dynamic response of certain frequency channels to deviations from the threshold.

To imitate masking effects, the selection of the same channel for stimulation a certain number of times may be used as a control signal to reduce the probability of future selection of the channel. The dynamics of this masking effect may be easily adjustable by changing the parameters of the algorithm. Cross channel masking effects may be implemented, for example, by using a control matrix which allows information about the selection history of one channel to be used to affect other channels.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method comprising:
   determining an amplitude of each of a multiplicity of stimulation signals each corresponding to a distinct channel included in an implantable stimulation system;
   using said amplitudes of said stimulation signals to determine a plurality of probabilities, each probability within said plurality of probabilities corresponding to a different stimulation signal within said multiplicity of stimulation signals;

obtaining a plurality of random numbers, each random number within said plurality of random numbers corresponding to a different stimulation signal within said multiplicity of stimulation signals;

identifying each stimulation signal included in the multiplicity of stimulation signals that has a corresponding probability greater than a corresponding random number;

selecting the identified stimulation signals to be applied to a patient during a stimulation frame; and applying the selected stimulation signals to the patient during the stimulation frame through a subset of a total number of channels in the implantable stimulation system.

2. The method of claim 1, wherein said step of determining said amplitude of each of said multiplicity of stimulation signals comprises determining an envelope for each of said multiplicity of stimulation signals.

3. The method of claim 1, wherein said step of using said amplitudes of said stimulation signals to determine said plurality of probabilities further comprises:

summing said amplitudes of said stimulation signals; and computing said probability of said each of said stimulation signals by dividing each of said amplitudes by said sum of said amplitudes and multiplying a result of said division by a number equal to the subset of the total number of channels in the implantable stimulation system.

4. The method of claim 1, wherein the subset of the total number of channels through which the selected stimulation signals are applied comprises at least one channel through which a stimulation signal has not previously been applied during said stimulation frame.

5. The method of claim 1, further comprising:

adjusting said probabilities of one or more of said stimulation signals based on one or more center frequencies of one or more channels within said total number of channels.

6. The method of claim 1, wherein said implantable stimulation system comprises an implantable cochlear stimulation system.

7. The method of claim 1, wherein said implantable stimulation system comprises at least one or more of a spinal cord stimulation system and a deep brain stimulation system.

* * * * *